(12) United States Patent
Truschel et al.

(10) Patent No.: US 7,246,619 B2
(45) Date of Patent: Jul. 24, 2007

(54) SNORE DETECTING METHOD AND APPARATUS

(75) Inventors: William A Truschel, Monroeville, PA (US); Winslow K Duff, Export, PA (US); Robert Wheeler, Verona, PA (US); Andrew Shissler, Delmont, PA (US)

(73) Assignee: RIC Investments, LLC, Wilmington, DE (US)

( * ) Notice: Subject to any disclaimer, the term of this patent is extended or adjusted under 35 U.S.C. 154(b) by 225 days.

(21) Appl. No.: 10/265,845

(22) Filed: Oct. 7, 2002

(65) Prior Publication Data

US 2003/0066529 A1 Apr. 10, 2003

Related U.S. Application Data

(60) Provisional application No. 60/328,680, filed on Oct. 10, 2001.

(51) Int. Cl.
*A61M 16/00* (2006.01)
*A62B 7/04* (2006.01)
*F16K 31/26* (2006.01)

(52) U.S. Cl. .......................... 128/204.26; 128/204.18; 128/204.21; 128/848

(58) Field of Classification Search ............... 128/848, 128/202.22, 204.18, 204.21, 204.22, 204.23, 128/204.26, 205.23
See application file for complete search history.

(56) References Cited

U.S. PATENT DOCUMENTS

| | | | |
|---|---|---|---|
| 5,199,424 A | 4/1993 | Sullivan et al. | |
| 5,203,343 A | 4/1993 | Axe et al. | |
| 5,245,995 A | 9/1993 | Sullivan et al. | |
| 5,259,373 A | 11/1993 | Gruenke et al. | |
| 5,458,137 A | 10/1995 | Axe et al. | |
| 5,549,106 A * | 8/1996 | Gruenke et al. | 128/204.23 |
| 5,845,636 A * | 12/1998 | Gruenke et al. | 128/204.23 |
| 5,953,713 A * | 9/1999 | Behbehani et al. | 706/16 |
| 5,957,854 A * | 9/1999 | Besson et al. | 600/509 |
| 6,062,216 A * | 5/2000 | Corn | 128/204.23 |
| 6,085,747 A | 7/2000 | Axe et al. | |
| 6,138,675 A | 10/2000 | Berthon-Jones | |

* cited by examiner

*Primary Examiner*—Michael J. Hayes
*Assistant Examiner*—Michael Mendoza
(74) *Attorney, Agent, or Firm*—Michael W. Haas

(57) ABSTRACT

Method and apparatus for detecting disordered breathing in a patient and, in particular, to a method and apparatus for detecting patient snoring and/or for dynamically determining a snore detection threshold, and to a pressure support system and method of providing pressure support that uses this unique snore detection and/or snore detection dynamic adjustment technique to control the pressure provided to at patient.

24 Claims, 10 Drawing Sheets

SNORE DETECTING METHOD AND APPARATUS

CROSS-REFERENCE TO RELATED APPLICATIONS

This application claims priority under 35 U.S.C. § 119(e) from provisional U.S. patent application No. 60/328,680 filed Oct. 10, 2001, the contents of which are incorporated herein by reference.

BACKGROUND OF THE INVENTION

1. Field of the Invention

The present invention relates to a method and apparatus for detecting disordered breathing in a patient and, in particular, to a method and apparatus for detecting patient snoring and/or for dynamically adjusting a snore detection threshold, and to a pressure support system and method of providing pressure support that uses this unique snore detection and/or dynamic adjustment technique to control the pressure provided to a patient.

2. Brief Description of the Prior Art

It is known that may individuals suffer from disordered breathing during sleep. Obstructive sleep apnea (OSA), which is an example of such disordered breathing, is a condition in which sleep is repeatedly interrupted by an inability to breathe due to an obstructed upper airway segment. Obstruction of the airway is generally believed to be due, at least in part, to a general relaxation of the muscles which stabilize the upper airway segment.

Those afflicted with OSA experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of OSA include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete obstruction of the airway, it is also known that adverse effects, such as arousals from sleep, can occur where there is only a partial obstruction of the airway. Partial obstruction can result in shallow breathing referred to as a hypopnea. Other types of disordered breathing are upper airway resistance syndrome (UARS) and vibrations in the airway, such as vibrations of the pharyngeal wall, commonly referred to as snoring. It is known that snoring can accompany closure of the airway leading to UARS, hypopnea, or apnea. Thus snoring provides an indicator that the patient is experiencing abnormal breathing.

It is known to treat such disordered breathing by applying a continuous positive air pressure (CPAP) to the patient's airway. This positive pressure effectively "splints" the airway; thereby maintaining an open passage to the lungs. It is also known to provide a positive pressure therapy in which the pressure of gas produced in the patient's airway varies with the patient's breathing cycle, or varies with the patient's effort, to increase the comfort to the patient. This pressure support technique is referred to a bi-level pressure support, in which the inspiratory positive airway pressure (IPAP) is higher than the expiratory positive airway pressure (EPAP).

It is further known to provide a positive pressure therapy in which a continuous positive pressure is provided to the patient, and where the level of this pressure is automatically adjusted based on the detected conditions of the patient, such as whether the patient is snoring or experiencing an apnea, hypopnea or a change in upper airway resistance. This pressure support technique is referred to as an auto-titration pressure support device, because the pressure support device seeks to provide a pressure to the patient that is only as high as necessary to treat the disordered breathing.

Because, as noted above, snoring is an indicator of a partially collapsed or obstructed airway, with the collapse or obstruction usually occurring in the throat or nasal cavities, a snore detector is used to determine the necessary pressure to treat the patient according to known methods. See, e.g., U.S. Pat. Nos. 5,203,343; 5,458,137 and 6,085,747 all to Axe et al., U.S. Pat. No. 5,259,373 to Gruenke et al., U.S. Pat. Nos. 5,199,424 and 5,245,995 both to Sullivan et al., and U.S. Pat. No. 6,138,675 to Berthon-Jones et al.

Many of these known auto-titration systems having snore detecting capability are susceptible to false snore indications because they do not take into consideration the background noise and other noise in the detecting system. In some cases, the snore detector is equipped with a preset background noise threshold value or preset footprints of a signal corresponding to a snore pressure wave. These preset values are then compared to an electrical representation of the snore pressure wave. However, because the threshold value and footprints are preset, these methods do not take into account dynamic background noise and could erroneously register a false snore.

SUMMARY OF THE INVENTION

Accordingly, it is an object of the present invention to provide a snore detector and pressure support system using such a snore detector that overcomes the shortcomings of conventional snore-based auto-titration pressure support systems.

It is a further object of the present invention to increase snore detection accuracy by providing a snore detection method and apparatus which receives and evaluates real data collected from the patient and a surrounding environment.

These objects are achieved according to one embodiment of the present invention by providing a method for detecting a snore in a patient that includes the steps of: (a) providing a pressure support system including a pressure sensor, (b) monitoring a pressure within the pressure support system indicative of a pressure at an airway of a patient and outputting a pressure signal indicative of the pressure, (c) filtering the pressure signal to obtain a filtered pressure signal that contains frequencies in a specified frequency range, (d) generating a threshold value, (e) comparing the filtered pressure signal to the threshold value, (f) detecting a first vibration responsive to the filtered pressure signal crossing the threshold value, (g) determining a benchmark period for the first vibration, (h) detecting a second vibration when a second, subsequent vibration in the filtered pressure signal exceeds the threshold value, (i) determining a second period for the second, subsequent vibration, (j) comparing the second period to the benchmark period to determine if the periods are consistent, and (k) declaring a snore responsive to the second period being consistent with the benchmark period. The present invention also contemplates providing and apparatus or snore detector that implements these steps to detect patient snore events.

These objects are also achieved according to one embodiment of the present invention by providing a method of dynamically determining a threshold value for a snore detector that generally includes the steps of (a) generating a pressure signal indicative of the pressure at an airway of a patient that includes frequencies in a qualifying range, and (b) calculating a threshold value that changes in response to background noise fluctuations based on the pressure signal. The present invention also contemplates providing and apparatus or snore detector that implements these steps to dynamically adjust a threshold used to detect patient snore events by a snore detection device.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

A. System Hardware Configuration

Figure 1:
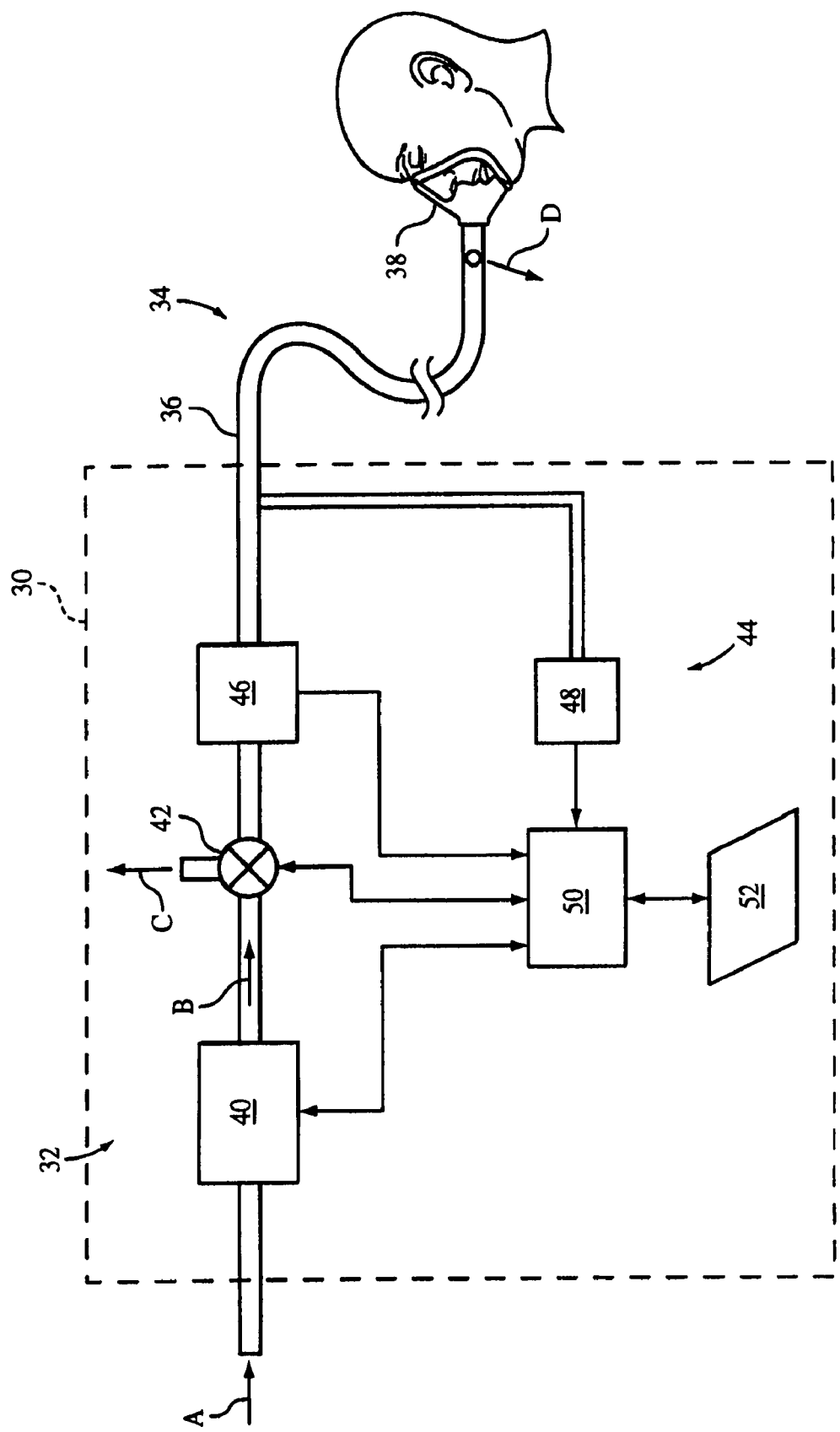
FIG. 1 is a schematic view of a pressure support system capable of implementing the snore detecting method according to the principles of the present invention.

The basic components of a pressure support system 30 that is adapted to implement the snore detection according to the principles of the present invention is discussed below with reference to FIG. 1. Pressure support system 30 includes a pressure generating system, generally indicated at 32, and a patient circuit 34, which includes a conduit 36 and a patient interface device 38. In the illustrated embodiment, pressure generating system 32 includes a pressure generator 40 and a pressure control valve 42 as the outlet of the pressure generator.

Pressure generator 40 receives the breathing gas from a source, as indicated by arrow A, and outputs the breathing gas, as indicated by arrow B, to patient circuit 34 at a pressure that is greater than atmosphere for delivery to the airway of a patient. In a preferred embodiment of the present invention, pressure generator 40 is a mechanical pressure generator, such as a blower, bellows or piston, that receives ambient air, for example, at an inlet from the gas source. Pressure control valve 42 controls the pressure of the flow of breathing gas delivered to the patient via the patient circuit by restricting the flow to the patient, by diverting flow from patient circuit 34, as indicated by arrow C, or a combination thereof.

The present invention further contemplates controlling the pressure of the flow of breathing gas delivered to the patient by controlling the operating speed of pressure generator 40, either alone or in combination with valve 42. Of course, valve 42 can be eliminated if operating speed alone is used to control the pressure of the flow of breathing gas delivered to the patient. Those skilled in the art can appreciate that other techniques for controlling the pressure of the flow of breathing gas delivered to the patient can be implemented in pressure support system 30, either alone or in combination to those discussed above. For example, a flow restricting valve (not shown) can be provided upstream of pressure generator 40 that controls the flow (arrow A) of gas to pressure generator 40, and, hence, the pressure of the flow of gas output for delivery to the patient.

Typically, the source of breathing gas is the ambient atmosphere, where its pressure is subsequently elevated for delivery to the patient by the pressure generating system. It is to be understood, that other sources of breathing gas are contemplated by the present invention, such as oxygen or an oxygen mixture from an oxygen source. It is to be further understood, that the present invention contemplates that pressurized air can be provided to the airway of the patient directly from a tank of pressurized air via the patient circuit without using a pressure generator, such as a blower, bellows or piston, to increase the pressure of the air. Of course, a pressure regulator, such as valve 42 would be required to control the pressure of the gas delivered to the patient. The important feature with respect to the present invention is that pressurized breathing gas is provided in the patient circuit for delivery to the patient, not necessarily the source or manner in which the pressurized breathing gas is generated.

Although not shown in FIG. 1, the present invention also contemplates providing a secondary flow of gas, either alone or in combination with the primary flow of gas (arrow A) from atmosphere to the pressure generator. For example, a flow of oxygen from any suitable source can be provided upstream to pressure generator 40 or downstream of the pressure generator in the patient circuit or at the patient interface device to control the fraction of inspired oxygen delivered to the patient.

In the illustrated embodiment, conduit 36 in patient circuit 34 has one end coupled to the output of the pressure generator 40 and another end coupled to patient interface 38. Conduit 36 is any tubing capable of carrying the gas flow from the pressure generator to the airway of the patient. Typically, a distal portion of the conduit 36 relative to pressure generator 40 is flexible to allow for freedom of movement of the patient. It is to be understood that various components may be provided in or coupled to patient circuit 34. For example, a bacteria filter, pressure control valve, flow control valve, sensor, meter, pressure filter, humidifier and/or heater can be provided in or attached to the patient circuit. Likewise, other components, such as muffler and filters can be provided at the inlet of pressure generator 40 and at the outlet of valve 42.

Patient interface 38 in patient circuit 34 is any device suitable for communicating an end of conduit 36 with the airway of the patient. Examples of suitable patient interface devices include a nasal mask, oral mask or mouthpiece, nasal/oral mask, nasal cannula, trachea tube, intubation tube, hood or full face mask. It is to be understood that this list of suitable interface devices is not intended to be exclusive or exhaustive.

In the single limb patient circuit of the present invention, exhaled gas from the patient typically exits the patient circuit via an exhaust vent 43, as indicated by arrow D. In the illustrated embodiment, exhaust vent 43 is provided on a distal portion of conduit 34. Depending on the tidal volume of the patient and the pressure delivered by pressure support system 30, a small percentage of the exhaled gas may travel back up the conduit into pressure support system 30 and may even, be exhausted to atmosphere through the gas inlet of the pressure generator and/or through a pressure control valve 42, if such a valve is being used with the pressure generator.

Typically, exhaust vent 43 is an orifice provided in the conduit that communicates the interior of the conduit with atmosphere, with no active control over the flow of gas from the system. It is to be understood, however, that a wide variety of exhaust devices and configurations are contemplated for use with the pressure generating system of the present invention. For example, U.S. Pat. No. 5,685,296 to Zdrojkowski et al. discloses an exhalation device and method where the exhalation flow rate through the device remains substantially constant over a range of pressures in the patient circuit. This exhalation device, which is commonly referred to as a plateau exhalation valve or PEV, is suitable for use with the pressure support system of the present invention.

As shown in FIG. 1, pressure support system 30 includes a monitoring system, generating indicated at 44 to monitor the flow and pressure of gas delivered to the patient. In the illustrated embodiment, monitoring system 44 includes an optional flow sensor 46 that measures a rate at which the breathing gas flows within patient circuit 34. It is to be understood that this sensor is optional because the snore detection technique described herein is based on the pressure within patient circuit 34 and not the flow therethrough. Nevertheless, if provided, the present invention contemplates that any suitable sensor, such as a conventional pneumatach, can be used for flow sensor 46. It is to be further understood that flow sensor 46, if provided, need not be coupled directly to conduit 36. On the contrary, the present invention contemplates the use of any sensor or a plurality of sensors that can quantitatively measure airflow in the patient circuit. For example, flow in the system can be measured at the patient interface device or can be measured or estimated from the motor or piston speed or from torque used to provide the elevated pressure by pressure generator 40. In short, the present invention contemplates any conventional technique for measuring the flow of gas delivered to the patient.

Monitoring system 44 includes a pressure sensor 48 that detects the pressure of the gas at the patient. In the illustrated embodiment, pressure sensor 48 is in fluid communication with patient interface device 38 via a conduit 36. It is to understood, however, that the patient pressure can be measured at patient interface device 38. Examples of a suitable pressure sensor includes a piezo electric pressure sensor, such as the SM5652 model available from Silicon Microstructures, the BP01 model available from Senyson, the MPX2010DP model available from Motorola, or any other sensor having, a suitable response time. Pressure sensor 48 measures a pressure wave of a patient breath, converts the pressure wave to an electrical signal, and sends the electrical signal to a controller 50.

Controller 50 is preferably a microprocessor capable of implementing a stored algorithm, receiving the monitored variables (including the signal from pressure sensor 48) and controlling pressure generating system 32 based on these signals. Of course, controller 50 includes the necessary memory and processing capability to implement the snore detecting features of the present invention discussed in detail below. A suitable controller 50 includes the AT-91 Arm Thumb brand of microcontroller, the PIC brand of processor, the Motorola 68HC16 brand of processor, or any other suitable computer or controller 50 capable of performing multiple functions. Controller 50 evaluates the signal from pressure sensor 48 and increases or decreases the pressure of the flow of breathing gas delivered to the patient by increasing or decreasing the operating speed of pressure generator 40, restricting or dilating the control valve 42, or using both the pressure generator 40 and the control valve 42 in concert.

The present invention contemplates that pressure support system 30 includes an input/output interface 52 for communicating, information, data and/or instructions between a user and controller 50. Examples of common input/output interfaces suitable for this purpose include a keypad and display. Other communication techniques, either hard-wired or wireless, are also contemplated by the present invention. For example, the present invention contemplates providing a smart card terminal, RS-232 port, RF link, modem (telephone, cable or other) as an input/output interface for communicating information, data, instructions, or other items, to and from the controller. In short, any conventional technique for exchanging information, data, instructions, or other items with the controller are contemplated by the present invention.

Figure 2:
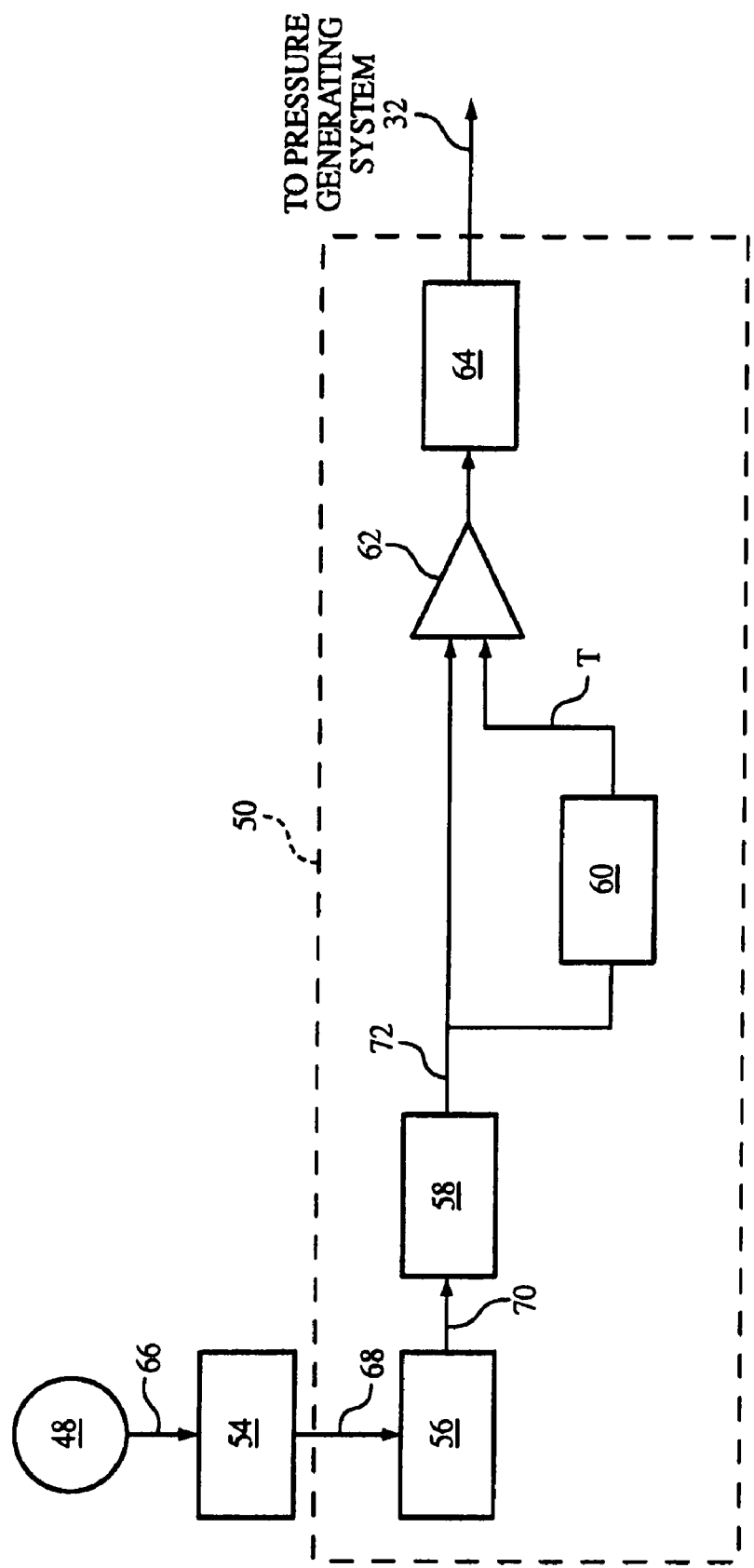
FIG. 2 is a schematic view of a snore detector in the pressure support system of FIG. 1 according to the principles of the present invention.

As shown generally in FIG. 2, the snore detecting components of pressure support system 30 includes an audio receiver, such as a microphone or pressure sensor 48, an analog filter 54, an analog-to-digital converter 56, a digital band pass filter 58, a comparator 62, and a snore analysis device 64. Each of these items and the remaining reference numerals in FIG. 2 are discussed in greater detail below. It should be noted that analog-to-digital converter 56, digital band pass filter 58, comparator 62, and snore analysis device 64 are preferably implemented within controller 50 by suitable programming. However, or one or more of these functions can be accomplished by dedicated circuitry.

B. Snore Detection

As noted above, when an airway of a patient is constricted or collapsed, one symptom may be vibrations in the patient tissues which are detected by audible snoring. It is, therefore, important to detect a snore, so that a constricted or collapsed airway can be opened by the appropriate application of a positive pressure to the airway of the patient. With this objective in mind, the present invention uses pressure sensor 48 as a microphone, because pressure sensor 48 is capable of converting a snore pressure wave into a proportional analog signal.

Controller 50 is programmed to function as a snore detection device that, in essence, "listens" for snores imposed on the pressure signal from pressure sensor 48. According to the present invention, the patient is deemed to be experiencing a snore event if the following criteria are met: (1) the energy level of the pressure sensor signal is greater than the normal background noise in the patient circuit and snore detection components, and (2) these deviations above the normal background noise occur at a consistent frequency that is in a range that is characteristic of human snoring. Both of these requirements must be met before the controller will declare a valid snore event, and each is discussed in turn below.

1. Energy Level Analysis of the Pressure Signal

It is necessary to first digitize the analog signals from pressure sensor 48 for computer analysis. Referring again to FIG. 2, an analog signal 66 produced by pressure sensor 48 is filtered by the analog filter 54, such as a low pass filter that filters frequencies generally significantly greater than a sampling frequency. Filtered analog signal 68 is then transmitted to the analog-to-digital converter 56 and converted into a digital signal 70.

The analog-to-digital conversion should occur at a suitable frequency for detecting audible snore frequencies. One way of converting the filtered analog signal 68 into the digital signal 70 is to use a successive approximation register or a delta-sigma converter, such as the MCP 3202 brand analog-to-digital converter 56 commercially available from MICROCHIP. The sample time should be sufficiently small to satisfy Nyquist's criterion for the highest qualifying frequency. The greater number of bits used in the conversion will increase the flexibility of the present invention, but both 10-bit and 12-bit designs have been successful.

Digital signal 70 is then passed, relayed, or transmitted to a digital band pass filter 58, which is preferably implemented by a floating or fixed point computer contained in the controller 50. Digital band pass filter 58 filters digital signal 70 to obtain a filtered digital signal 72 containing qualifying frequencies in a range of about 40-160 Hz. The approximate qualifying frequency range represents the approximate range of frequencies produced during snoring and takes into account factors, such as the age, gender, or health of a patient. It should be noted that the sound pressure variations, unless they are uncomfortably loud, are generally small in amplitude, such as much less than one centimeter $H_2O$. Other signals with frequencies outside the qualifying range may also, interfere with filtered digital signal 72 because the other signals have large amplitudes and are not completely attenuated by digital band pass filter 58. Furthermore, other noise signals that are barely perceptible, but within the qualifying range, may be obtrusive. Digital band pass filter 58 set to reject frequencies outside of the qualifying range will generally filter the DC, CPAP, and bi-level pressures from the digital signal.

In addition to filtering unwanted audible frequencies, the present invention contemplates modifying digital band pass filter 58 to further limit the qualifying range to a specific frequency range tailored for a particular patient. For example, it has been found that snoring males tend to produce lower audible frequencies and snoring females tend to snore at higher audible frequencies. Moreover, the present invention can be used to archive sample snores for a given patient and further tailor the qualifying frequency range to an even narrower, individualized qualifying range of frequencies.

With continuing reference to FIG. 2, a threshold value T is generated by threshold generator 60. This threshold level must be set at a level that above the normal background noise in the pressure support system, so that normal noise is not erroneously deemed to be snore event. It can be appreciated that any number of a variety of techniques can be used to set this threshold to an appropriate level. For example, U.S. Pat. Nos. 5,259,373 and 6,138,675 disclose a technique for setting a preset threshold value T. The present invention further contemplates averaging or integrating the values of the filtered digital signal 72 or averaging peaks of the filtered digital signal 72 and processing the average, volume or peak level to provide an approximate threshold value. However, in a preferred embodiment of the present invention, threshold value T is determined by effectively causing the controller the "surf" a fixed level above the peaks of the background signal to maintain the threshold value T at a high enough level to account for background noise, but at a low enough level to detect even relatively quiet snore events. According to a presently preferred embodiment of the present invention, threshold value T is dynamically adjusted based on changes in the patient pressure, background noise and patient noises.

Figure 3:
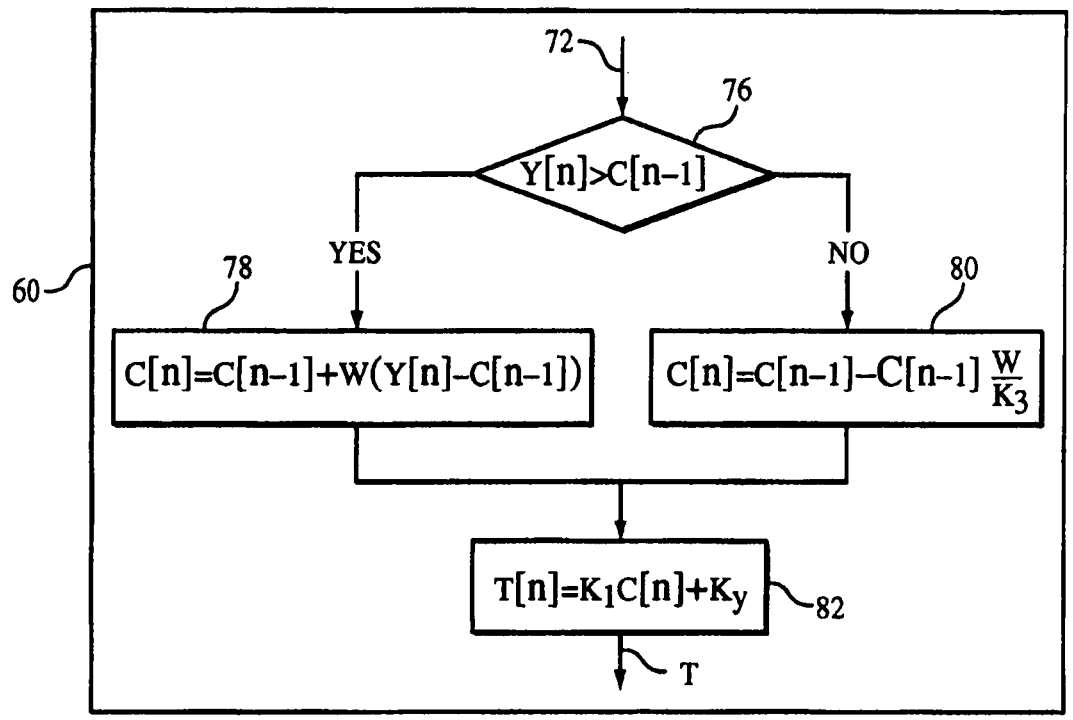
FIG. 3 is a flowchart of a threshold generator algorithm used to set a dynamic threshold T for the snore detector according to the present invention.
Figure 4:
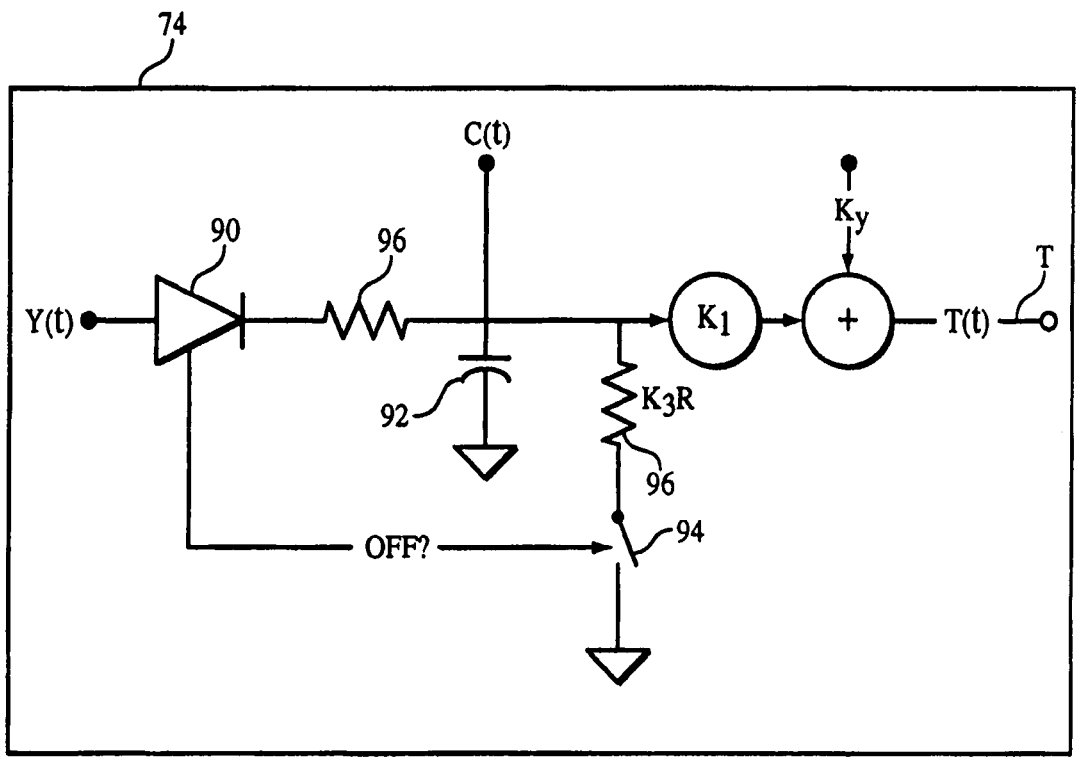
FIG. 4 is a schematic view of a circuit that is approximately equivalent to the threshold generator algorithm shown in FIG. 3.

In a preferred embodiment of the present invention, as shown generally in FIGS. 3-6, threshold generator 60 generates a changing threshold value T using an algorithm and a stream of input data from filtered digital signal 72. The algorithm used by threshold generator 60 is shown in FIG. 3, and is the equivalent of an RC circuit with separate charge and discharge paths, as shown in FIG. 4. As noted above, the threshold generator produces a threshold T that varies with the background noise of the pressure support system and that is above this noise. This threshold value is used as a first criteria for determining when a patient's breathing pattern is indicative of a snore event.

Referring to FIG. 3, in step 76, during a current processing cycle n, a current input signal Y[n] is compared to C[n−1], which is a level proportional to the threshold value T from a pervious processing cycle (n−1). In FIG. 3, W is defined as a charge constant=$1/F_sRC$, where $1/F_s<2RC$ and $F_s$ is the sampling frequency. $K_1$ is defined as the threshold constant and is set to approximately 3. $K_3$ is defined as the ratio of charge to discharge rate and is set to approximately 1. For pressures less than approximately 15 cm $H_2O$, an offset $K_y$ of approximately 0.05 cm $H_2O$ may be used. For pressures which are higher, an offset of approximately 0.065 cm $H_2O$ may be used. Each offset may be scaled by a fixed point scale factor. For an $F_s$ of approximately 500 Hz and an RC of approximately 0.5, W is approximately equal to 0.004 and is scaled by the fixed point scale factor. Steps 78 and 80 indicate how C[n] for the current processing cycle is calculated depending on the result of the comparison in step 78. In step 82, a new value for threshold T for the current processing cycle is calculated using the newly determined value of C[n], $K_1$, and $K_y$.

Referring to FIG. 4, circuit 74 generally describes the algorithm shown in FIG. 3. In other words, the algorithm shown in FIG. 3 attempts to model the performance of circuit 74. It is to be understood, that the algorithm shown in FIG. 3 is executed using a computer. Thus, the inputs and variables are expressed as a function of the processing cycle n, rather than as a function of time (t) as in FIG. 4. For this reason, Y[n] in FIG. 3 approximates Y(t) in FIG. 4, C[n] approximates C(t), and the threshold vale T[n] approximates T(t). The approximation approaches equivalence as $F_s$ increases and diode 90 is considered ideal. Circuit 74 includes an ideal diode 90, a capacitor 92, a switch 94, and resistors 96. $K_y$ is defined as an offset added to a calculated threshold value, T(t) is defined as the calculated threshold value, C(t) is an intermediate function that is proportional to the previous threshold value, and Y(t) is defined as the filtered digital signal 72.

In simple terms, the diode in circuit 74 determines whether or not to increase or decrease the threshold value based on the input pressure signal Y(t). When the input signal is greater than C(t), which is a value proportional to the threshold T, the threshold in increased slowly according to the value of resistor 96 and capacitor 92. When the input signal is less than C(t), the threshold is slowly decreased toward zero according to the value of resistor 96, capacitor 92, and constant $K_3$. This combination of elements is used in the present embodiment of the invention to provide a signal, T(t), that is a fixed offset, $K_y$, above the approximate peaks of the background noise. T[n], Y[n], and C[n] in FIG. 3 are simply digital approximations to the analog signals in FIG. 4.

Figure 5:
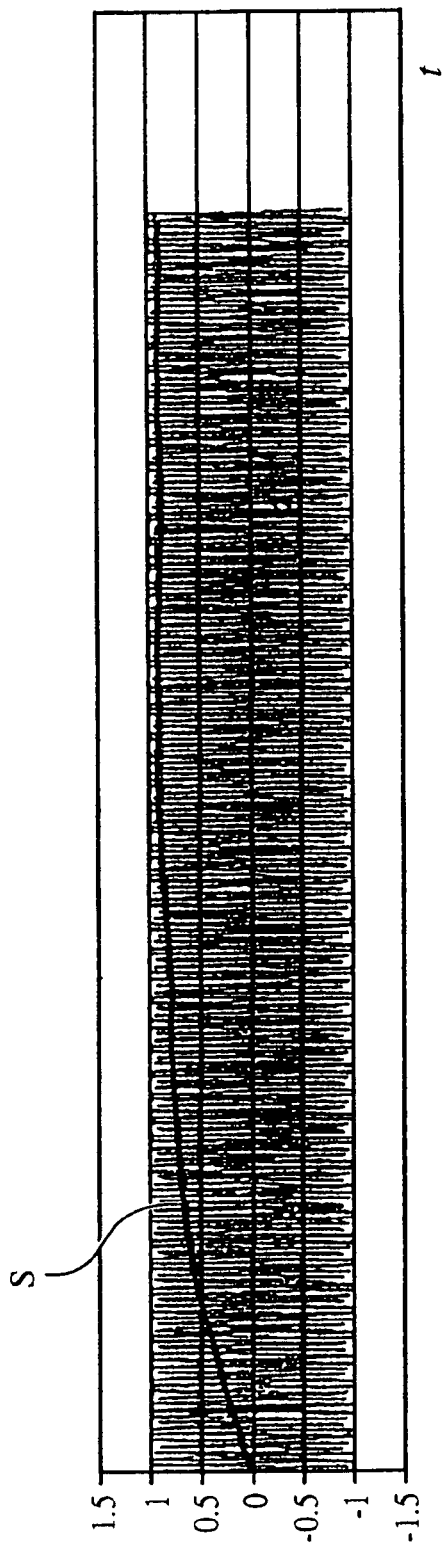
FIG. 5 is a graphical depiction of the output of the threshold generator represented in FIGS. 3 and 4 excited with a normalized sinusoidal input.

FIG. 5 shows an example of what an output S of threshold generator 60 according to the present invention looks like when excited with a 50 Hz normalized sinusoidal input and excluding the offset value $K_y$. As shown in FIG. 5, output S, starting from zero, increases over time and eventually plateaus near the peak of the sine wave.

Figure 6:
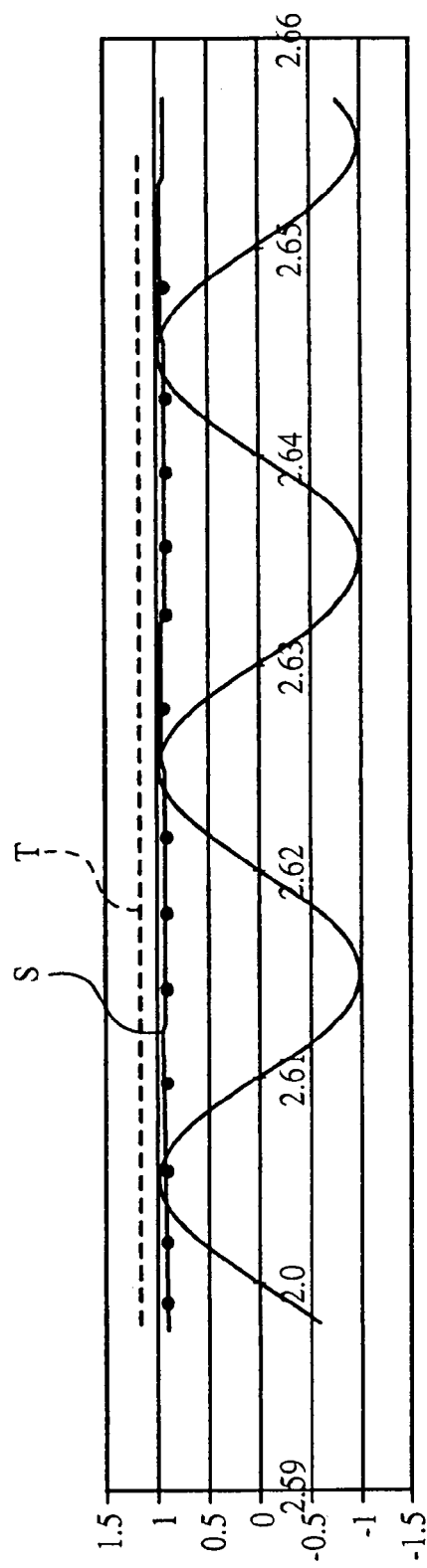
FIG. 6 is a more detailed graphical depiction of the output shown in FIG. 5.

FIG. 6 is a plot of the output S that shows, in greater detail, this output produced by threshold generator 60 when excited with the 50 Hz normalized sinusoidal input. It can be appreciated from this figure, that in producing value S, threshold generator 60 essentially monitors the peaks of filtered digital signal 72. The steady state response S is independent of the frequency of filtered digital signal 72, with the exception of the amount of ripple, and is an approximate indication of the peak. Threshold value T is then set at approximately ½₀ of a centimeter $H_2O$ above steady state line S shown in FIG. 6 by adding offset $K_y$ to signal S.

The dynamic threshold value T produced by the threshold generator 60 according to the present invention is more advantageous than a preset threshold value because a preset threshold value does not take into account unanticipated background noise. Threshold value T according to the present invention also differs from a threshold value which is completely time dependent on filtered digital signal 72, because the steady state S changes very slowly over time. This is perhaps best shown in FIG. 7, which is a graphical depiction of threshold value T changing over time as an actual pressure signal 72 from a snoring patient is analyzed.

Figure 7:
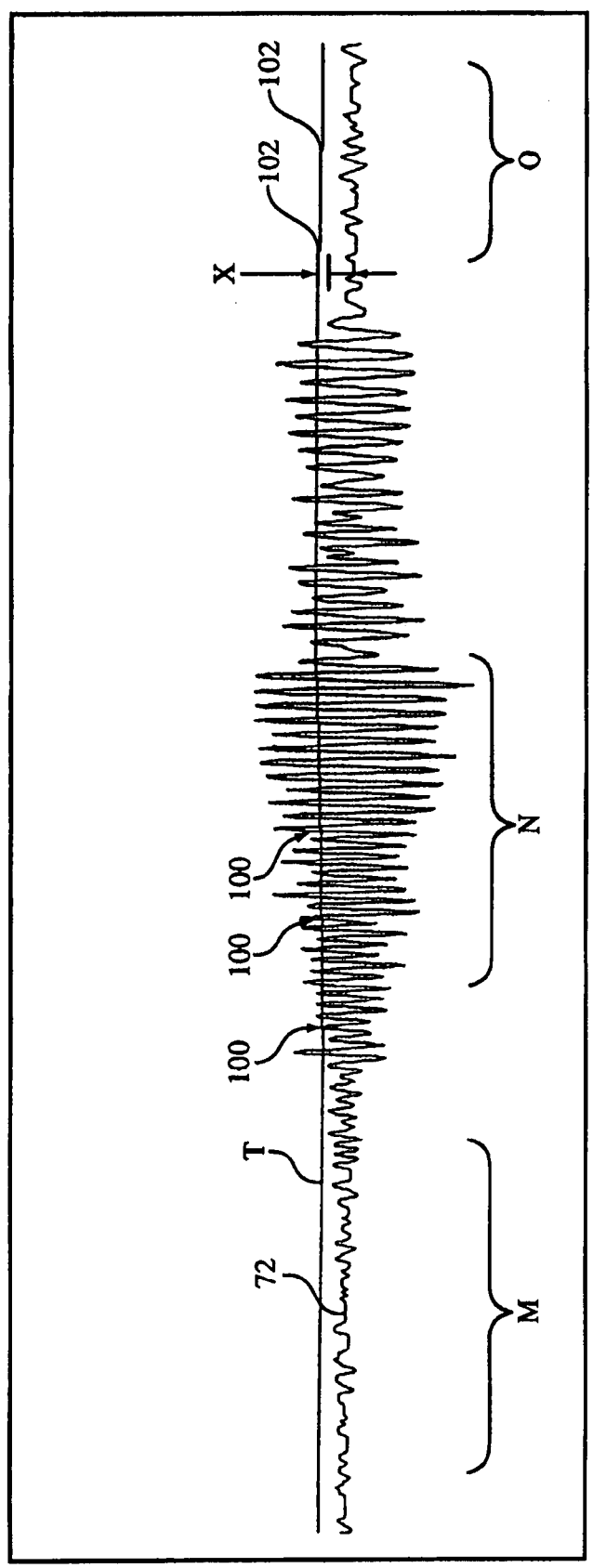
FIG. 7 is a graphical depiction of the threshold value changing over time as the pressure signal input to the threshold generator changes.

As shown in this figure, in region M, pressure signal 72 is relatively stable and has a relative low value. In this region, the fluctuations in the pressure signal are typically due to noise. In region N, the period during which the snore occurs, the magnitude of pressure signal 72 varies more widely than in region M. It can be said that, over a common time period, the energy of the pressure signal, which can also be considered as the area of the signal above zero, is greater in region N than in region M. Thus, the input (Y(t) or Y[n]) to the threshold generator is greater in region N than in region M. This results in a relatively slow, but steady state increase in threshold value T. These increases are identified by numerals 100 in FIG. 7. It can be appreciated that if the pressure signal 72 provided to threshold generator 60 remains at this relatively high magnitude for a period of time, the level of threshold signal T will be increased above the value it has prior to region M. This overall increase is shown in FIG. 7 as distance x.

Of course, a similar, yet opposite effect occurs between region O and region N, where the magnitude of pressure signal 72 is relatively stable in region O. As a result, there is a relatively slow, but steady decrease in threshold value T, as indicated at 102 in FIG. 7.

Figure 8:
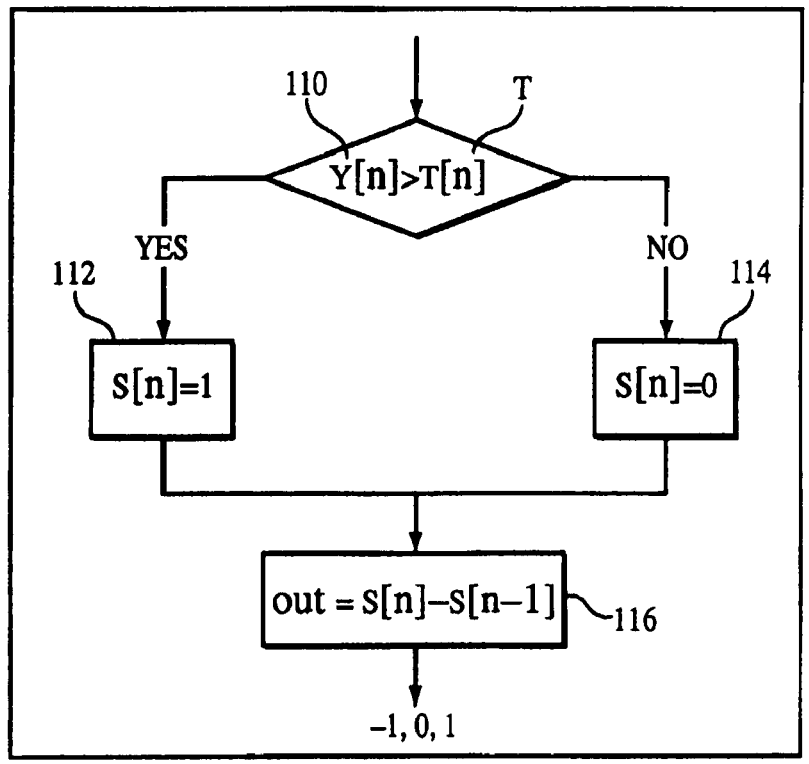
FIG. 8 is a flowchart illustrating the operation of a snore comparator according to the present invention.

Once threshold value T has been calculated, the next step in the snore detection process is to compare filtered digital signal 72 to the threshold value, preferably via comparator 62 shown in FIG. 2. The steps performed by comparator 62 are shown in FIG. 8, and FIG. 9 and illustrates a graphical depiction of the operation of the comparator.

In short, the output of snore comparator 62, generally has a value of zero (0) when signal 72 is above and below threshold value T, a value of one (1) when the signal 72 crosses the threshold T in a positive direction, and a value of negative one (−1) when signal 12 crosses the threshold T in a negative direction.

In step 110, comparator 62 compares filtered digital pressure signal 72 Y[n] to threshold value T[n] for that processing cycle n to determine whether signal 72 has crossed threshold T. For example, if signal 72 is greater than threshold T, a threshold crossing flag S[n] is set to 1 in step 112. If on the other hand, signal 72 is less than threshold T, a threshold crossing flag S[n] for that processing cycle is set to 0 in step 114. In step 116, comparator 64 assigns a value to digital filtered pressure signal 72 to indicate whether this signal is crossing the threshold value in an increasing direction (out=1) or in a decreasing direction (out=−1). After each crossing, the threshold crossing flag S[n] resets to zero in the next cycle because the prior value of the flag is subtracted from its current value in step 116.

Figure 9:
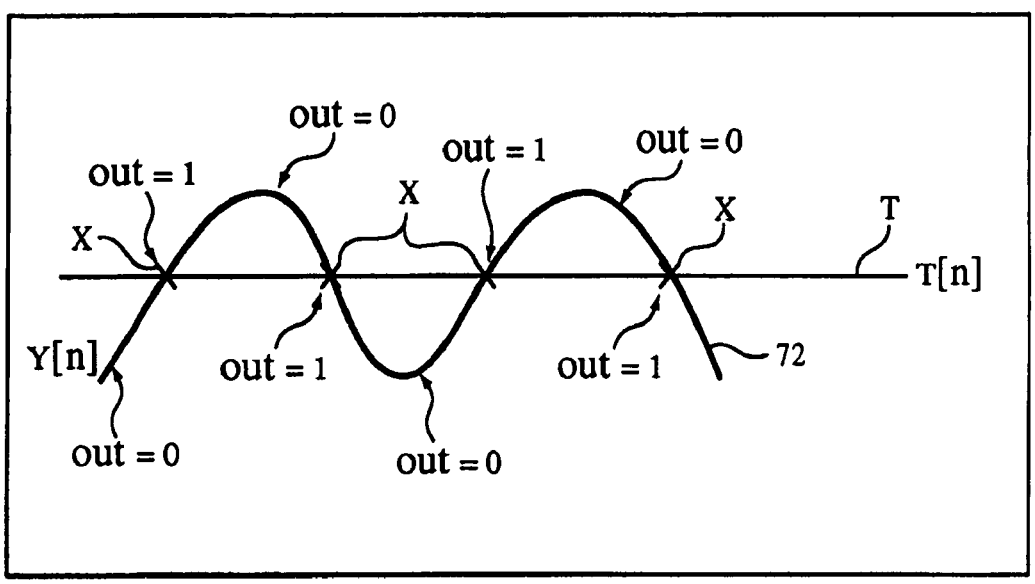
FIG. 9 is a graphical depiction of the operation of the snore comparator shown in FIG. 8.

FIG. 9 graphically illustrates the output of step 116 based on the crossings between filtered digital signal 72 and threshold value T. That is, FIG. 9 shows filtered digital signal 72 repeatedly crossing threshold value T at a plurality of crossings X. A crossing is defined as a point of intersection between threshold value T and filtered digital signal 72 (Y[n]). As noted above, the direction of each crossing is determined depending on the trend of filtered digital signal 72.

2. Frequency Analysis of the Pressure Signal

As noted above, the snore detector of the present invention does more that look for situations where the patient pressure signal crosses a threshold. If this were the case, any "abnormal" change in pressure that is not otherwise filtered out by filters 54 and 58, such as a cough, may produce an erroneous snore event indication. For these reasons, the present invention also monitors the frequency at which the patient pressure crosses the threshold, and only declares a snore event if these crossings are repetitive in a manner that is characteristic of human snoring.

In other words, the frequency at which pressure signal 72 crosses threshold value T must first be within a range sufficient to qualify as a snore. For example, the present invention contemplates "listening" for a snore by first checking for vibrations in pressure signal 72 within a broad range of 40 to 160 Hz. However, after the first high energy vibration, i.e., vibration in pressure signal 72 that exceeds threshold T, in order to qualify as a true snore, the subsequent vibrations must be within a more narrow frequency band centered around the frequency band of the first high energy vibration. For example, if the first high-energy vibration occurred at a frequency of 50 Hz, the subsequent vibrations must occur in a frequency band from 40 to 60 Hz, i.e., ±10 Hz around the frequency band of the first high-energy pressure signal vibration. In the illustrated exemplary embodiment, this analysis of the frequency to the patient pressure signal is performed by snore analysis device 64 in controller 50 based on the output of comparator 62.

Figure 10:
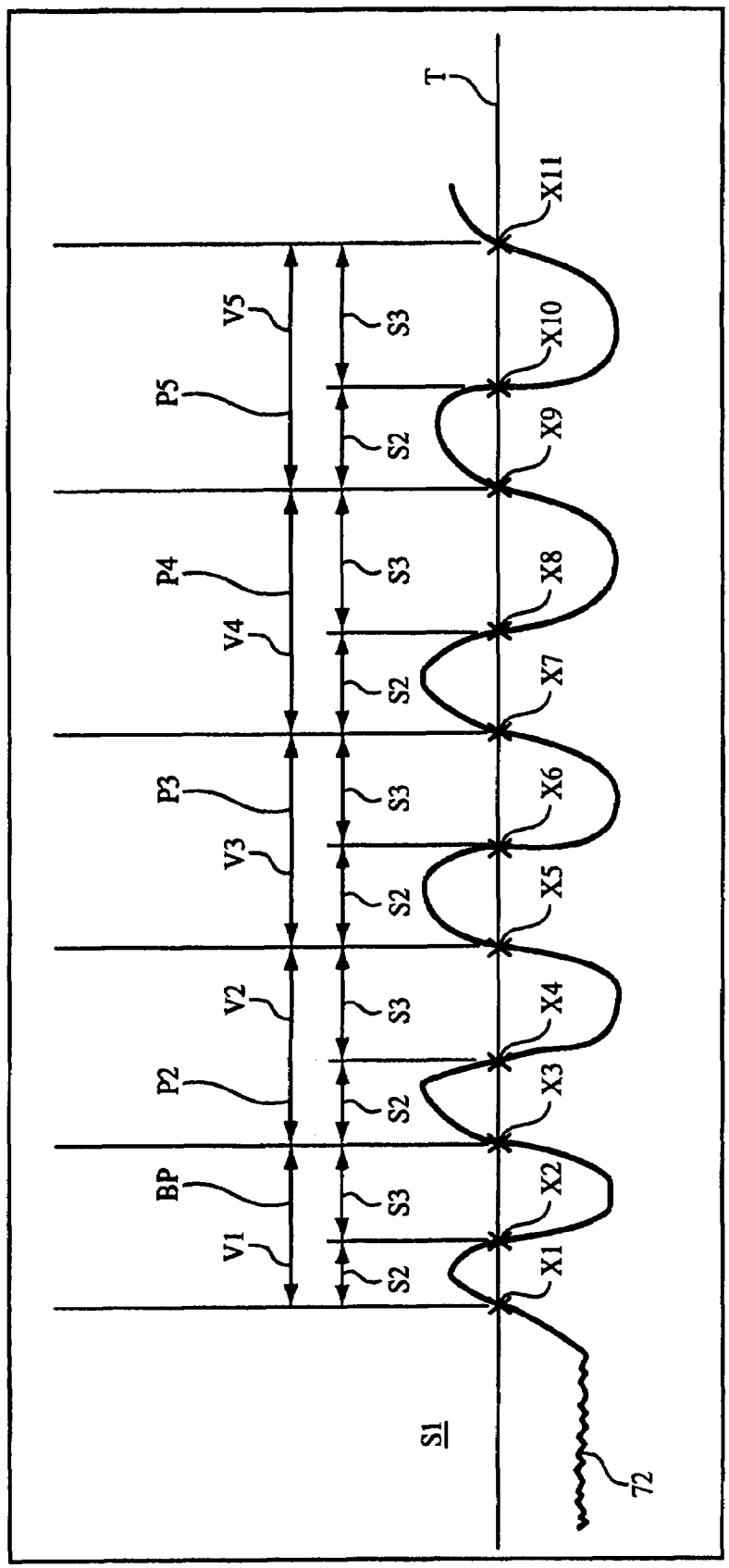
FIG. 10 is an enlarged view of a filtered digital patient pressure signal crossing a threshold.

The frequency analysis concept according to the principles of the present invention is illustrated in FIG. 10, where a plurality of crossing X1-X11 of pressure signal 72 and threshold value T are shown. A vibration V1-V5 of pressure signal 72 is defined as three consecutive crossings of the signal 72 with respect to the threshold value T. Once there are three consecutive crossings and a vibration is counted, the period and frequency of the vibration are evaluated. For example, as shown in FIG. 10, the filtered digital signal 72 first exceeds threshold value T in a positive direction at crossing X1, then in the negative direction at crossing X2, and once again in the positive direction at crossing X3. At this point, a first vibration V1 is counted, and a benchmark period BP corresponding to the first vibration VI is calculated.

Figure 11:
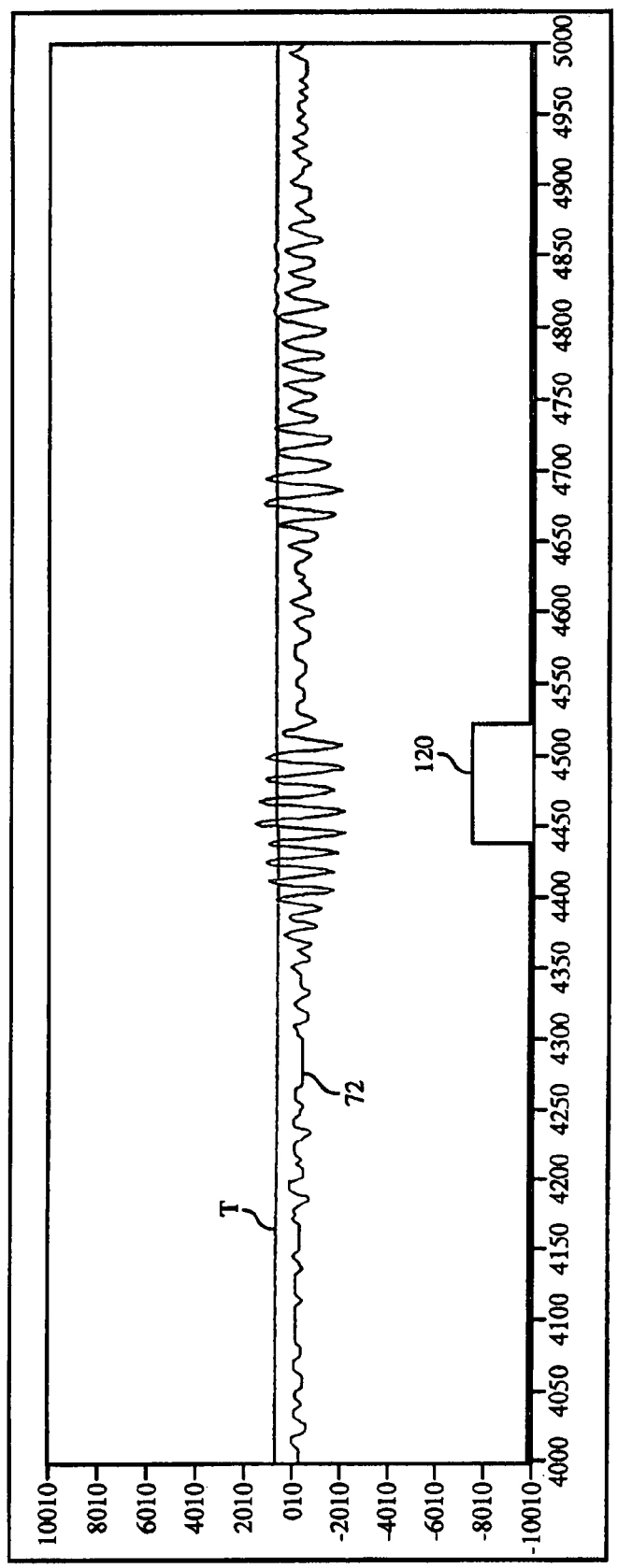
FIGS. 11 and 12 are a graphical depictions of a filtered digital patient pressure signal crossing threshold value T and the detection of snore events based on this threshold crossing.

The last crossing X3 of the first vibration V1 is the first crossing for a possible second vibration V2. If filtered digital signal 72 subsequently crosses the threshold value T three times, once in the positive direction at crossing X3, once in the negative direction at crossing X4, and once again in a positive direction at crossing X5, a second vibration V2 is counted, and a second period P2 corresponding to the second vibration V2 is calculated. The second period P2 of the second vibration V2 is then compared to the benchmark period BP to determine if the two periods P2, BP are consistent, such as within approximately plus or minus 8 msec. If the two periods P2, BP are comparable, then subsequent vibrations V3-V5 are examined as described above, and a period P3-P5 corresponding to each subsequent vibration V3-V5 is calculated and individually compared to the benchmark period BP. If the subsequent periods P3-P5 correspond to the benchmark period BP, with three or more subsequent periods being preferred, then a snore 120 is registered, as shown in FIG. 11. It should be noted that the threshold for declaring whether the second period is consistent with the first period need not be fixed and it can be set to other values, such as plus or minus 6 msec, depending on the desired snore detection accuracy and reliability.

In a present embodiment of the present invention, snore analysis device 64 signals pressure generating system 32 to increase the pressure of the flow of breathing has provided to the patient based on the detection of snore events, and vibration counting is reset. If a period P2-P5 of a subsequent vibration V2-V5 is not consistent with the benchmark period BP, then vibration counting is reset and the period of the subsequent non-consistent vibration becomes the new benchmark period.

Figure 12:
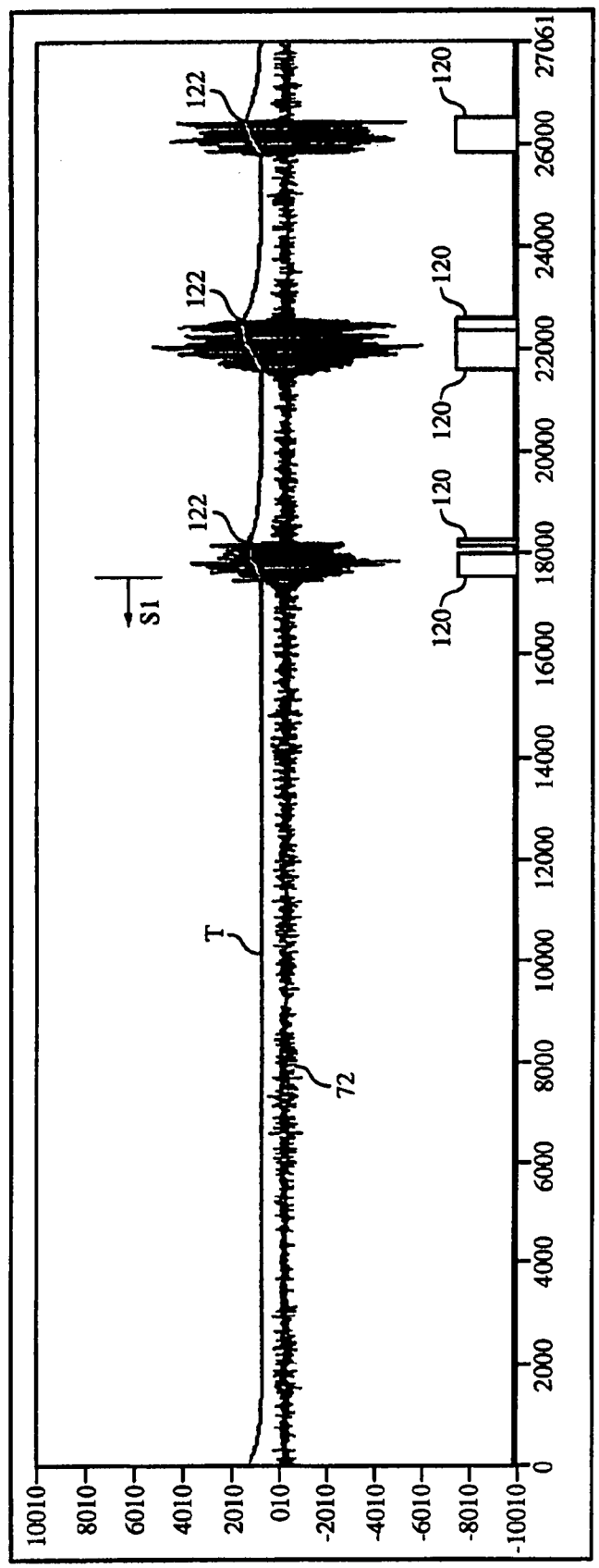

Referring again to FIG. 10 and to FIGS. 12 and 13, filtered digital signal 72 is below the threshold value T in a first state S1. When filtered digital signal 72 exceeds the threshold value T in a positive direction, the crossing X1 represents a change in state from the first state S1 to a new state S2. At this point, the algorithm waits for a crossing X2 of filtered digital pressure signal 72 in the negative direction. If a crossing X2 in the negative direction does not occur after some arbitrary maximum time period, the first crossing X1 is discarded and the algorithm returns to the first state S1.

If, however, there is a crossing X2 in the negative direction, the crossing X2 represents a change from the second state S2 to a third state S3. If another crossing X3 in the positive direction does not occur, the third state S3 defaults to the first state S1. However, if there is a crossing X3 in the positive direction, the state changes from the third state S3 to the second state S2, a first vibration V1 is counted, and the corresponding benchmark period BP is calculated. The algorithm once again waits for a crossing X4 in the negative direction. If a crossing X4 in the negative direction occurs, the state changes from the second state S2 to the third state S3 and a crossing X5 in the positive direction is anticipated. If there is a crossing X5 in the positive direction, the state changes from the third state S3 to the second state S2, a second vibration is counted V2, a second period P2 is calculated, and the second period P2 is compared to the benchmark period BP.

If the second period P2 does not correspond to the benchmark period BP, the first vibration VI is discarded and the second period P2 becomes the new benchmark period. If the second period P2 is consistent with the benchmark, but there is not another crossing X6 in the negative direction, the state changes from the third state S3 to the first state S1. If there is another crossing in the negative direction X6, however, the state changes from the second state S2 to the third state S3. This general process repeats until there are at least two and preferably four or more consecutive vibrations V1-V5 having consistent periods.

At this point, as shown in FIG. 11, a snore 120 is registered. Snore analysis device 64 then may prompt controller 50 to cause pressure generating system 32 to increase the pressure delivered to the patient. FIG. 12 also illustrates how threshold value T changes when vibrations are detected. For this reason, the threshold value T at the cessation 122 of the vibrations can be used to determine snore intensity.

Figure 13:
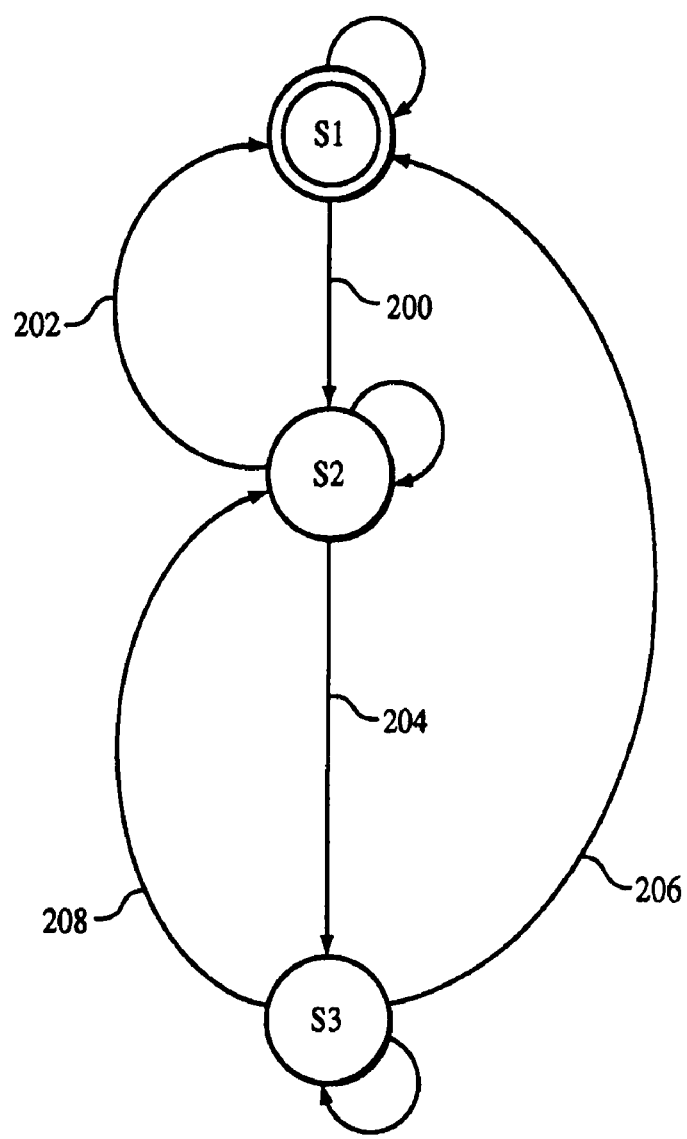
FIG. 13 is a state diagram illustrating the operation of the snore analysis device according to the principles of the present invention.

FIG. 13 is a state diagram illustrating the operation of the snore analysis device according to the principles of the present invention as discussed above. Therefore, a detailed description of this figure is omitted and reference is made to the above description of the operation of snore analysis device 64 and to FIG. 13.

The benefits of the present invention can be summarized as follows. First, threshold value T is based on the background noise and not a predetermined value. This prevents loud background noise, such as motor noise, from repeatedly tripping the snore detector. Secondly, the snore detector does not simply look for threshold crossings, but for a series of threshold crossings characteristic of human snoring. By this method, coughs, gags, sneezes, throat clearings, speech and other noises are generally rejected by the snore detector. Thirdly, by using the adaptive threshold described above, the movement of the threshold can be used as an indicator of snore severity.

The invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of detecting a snore in a patient comprising the steps of:
   (a) providing a pressure support system including a pressure sensor;
   (b) monitoring a pressure within the pressure support system indicative of a pressure at an airway of a patient and outputting a pressure signal indicative of the pressure;
   (c) filtering the pressure signal to obtain a filtered pressure signal that contains frequencies in a specified frequency range;
   (d) generating a theshold value;
   (e) comparing the filtered pressure signal to the threshold value;
   (f) detecting a first vibration from a plurality of vibrations defining a single snore event that occurs during respiratory cycle of such a patient responsive to the filtered pressure signal crossing the threshold value;
   (g) determining a benchmark period for the first vibration;
   (h) detecting a second vibration from the plurality of vibrations defining the single snore event when a second, subsequent vibration in the filtered pressure signal exceeds the threshold value;
   (i) determining a second period for the second, subsequent vibration;
   (j) comparing the second period to the benchmark period to determine if the periods are consistent; and
   (k) declaring a snore responsive to the second period being consistent with the benchmark period.

2. The method according to claim 1, further comprising:
   (l) detecting a third vibration subsequent to the second vibration when the filtered digital signal exceeds the threshold value;
   (m) determining a third period for the third vibration;
   (n) comparing the third period to the benchmark period to determine if the third period and the benchmark period are consistent;
   (o) detecting a fourth vibration responsive to the filtered digital signal exceeding the threshold value;
   (p) determining a fourth period for the fourth vibration; and
   (q) comparing the fourth period to the benchmark period to determine if the fourth period is consistent with the benchmark period, and wherein a snore is declared in step (k) responsive to the periods of the second, third, and fourth vibrations being consistent with the benchmark period.

3. The method according to claim 2, further comprising:
   (r) determining a benchmark frequency for a first vibration that exceeds the threshold;
   (s) comparing subsequent frequencies of corresponding subsequent vibrations with the benchmark frequency; and
   (t) declaring a snore if the subsequent frequencies are each consistent with the benchmark frequency.

4. The method according to claim 1, further comprising the steps of:
   (l) determining a benchmark frequency for a first vibration that exceeds the threshold;
   (m) comparing subsequent frequencies of corresponding subsequent vibrations with the benchmark frequency; and
   (n) declaring a snore if the subsequent frequencies are each consistent with the benchmark frequency.

5. The method according to claim 1, wherein generating a threshold value comprises the steps of:
   (1) processing the pressure signal to provide an approximation of average peak values for the pressure signal; and
   (2) adding an offset to the approximation of average peak values to produce the threshold value.

6. The method according to claim 5, wherein processing the pressure signal to provide the approximation of average peak values for the pressure signal, comprises:
   (i) calculating, during a current processing cycle n, a current approximation of average peak value C[n] as:

$$C[n]=C[n-1]+W(Y[n]-C[n-1]),$$

responsive to an approximation of the average peak value in a previous processing cycle C[n−1] being greater than the pressure signal during a current processing cycle Y[n], and
   (ii) calculating, during the current processing cycle, the current approximation of average peak value C[n] as:

$$C[n] = C[n-1] - C[n-1]\frac{W}{K_3},$$

responsive to the approximation of the average peak value in a previous processing cycle C[n−1] not being greater than the pressure signal during a current processing cycle Y[n], wherein W is charge constant for an RC circuit, and wherein $K_3$ is a ratio of a charge to discharge rate for the RC circuit.

7. The method according to claim 6, wherein adding the offset to the approximation of average peak values to produce the threshold value T[n] during a current processing cycle comprises processing the current approximation of average peak value C[n] as follows:

$$T[n]=K_1C[n]+K_y,$$

where $K_1$ and $K_y$ are constants.

8. The method according to claim 7, wherein a value of $K_y$ is selected based on the pressure signal.

9. The method according to claim 1, further comprising the step of adjusting the pressure provided by the pressure support system based on whether a snore is declared.

10. A method for monitoring snoring using variable threshold value for a snore detector comprising the steps of:
    (a) generating a pressure signal indicative of a pressure at an airway of a patient; and
    (b) processing the pressure signal to provide an approximation of average peak values for the pressure signal, wherein processing the pressure signal to provide the approximation of average peak values for the pressure signal, comprises:
       (1) calculating, during a current processing cycle n, a current approximation of average peak value C[n] as:

$$C[n]=C[n]+W(Y[n]-C[n-1]),$$

responsive to an approximation of the average peak value in a previous processing cycle C[n−1] being greater than the pressure signal during a current processing cycle Y[n], and
       (2) calculating, during the current processing cycle, the current approximation of average peak value C[n] as:

$$C[n] = C[n-1] - C[n-1]\frac{W}{K_3},$$

responsive to the approximation of the average peak value in a previous processing cycle C[n−1] not being greater than the pressure signal during a current processing cycle Y[n], wherein W is charge constant for an RC circuit, and wherein $K_3$ is a ratio of a charge to discharge rate for the RC circuit; and
  (c) adding an offset to the approximation of average peak values to produce the threshold value; and
  (d) using the threshold value and a measured parameter to determine whether such a patient is experiencing a snore.

11. The method according to claim 10, wherein adding the offset to the approximation of average peak values to produce the threshold value T[n] during a current processing cycle comprises processing the current approximation of average peak value C[n] as follows:

$$T[n]=K_1 C[n]+K_y,$$

where $K_1$ and $K_y$ are constants.

12. The method according to claim 11, wherein a value of $K_y$ is selected based on the pressure signal.

13. A snore detector comprising:
  (a) a pressure sensor adapted to detect a pressure indicative of a pressure at an airway of a patient and to output a pressure signal indicative thereof
  (b) means for filtering the pressure signal to obtain a filtered pressure signal that contains frequencies in a specified frequency range;
  (c) means for providing a threshold value;
  (d) means for comparing the filtered pressure signal to the threshold value;
  (e) means for detecting a first vibration from a plurality of vibrations defining a single snore event that occurs during respiratory cycle of such a patient responsive to the filtered digital signal exceeding the threshold value;
  (f) means for determining a benchmark period for the first vibration;
  (g) means for detecting a second vibration from the plurality of vibrations defining the single snore event responsive to a second vibration in the filtered pressure signal exceeding the threshold value;
  (h) means for determining a second period for the second vibration;
  (i) means for comparing the second period to the benchmark period to determine if the second periods and the benchmark period are consistent; and
  (j) means for declaring a snore responsive to the second period being consistent with the benchmark period.

14. The snore detector of claim 13, further comprising:
  (k) means for detecting a third vibration responsive to the filtered digital signal exceeding the threshold value;
  (l) means for determining a third period for the third vibration;
  (m) means for comparing the third period to the benchmark period to determine if the third period and the benchmark period are consistent;
  (n) means for detecting a fourth vibration responsive to the filtered digital signal exceeding the threshold value;
  (o) means for determining a fourth period for the fourth vibration; and
  (p) means for comparing the fourth period to the benchmark period to determine if the fourth period and the benchmark period are consistent, and wherein the means for declaring a snore responsive to the periods of the second, third, and fourth vibrations being consistent with the benchmark period.

15. The snore detector as claimed in claim 14, further comprising:
  (q) means for determining a benchmark frequency for a first vibration that exceeds the threshold; and (r) means for comparing subsequent frequencies of corresponding subsequent vibrations with the benchmark frequency; and
  (s) means for declaring a snore if the subsequent frequencies are each consistent with the benchmark frequency.

16. The snore detector according to claim 13, further comprising:
  (k) means for determining a benchmark frequency for a first vibration that exceeds the threshold;
  (l) means for comparing subsequent frequencies of corresponding subsequent vibrations with the benchmark frequency; and
  (m) means for declaring a snore if the subsequent frequencies are each consistent with the benchmark frequency.

17. The snore detector according to claim 13, wherein the means for providing a threshold value comprises:
  (1) means for processing the pressure signal to provide an approximation of average peak values for the pressure signal; and
  (2) means for adding an offset to the approximation of average peak values to produce the threshold value.

18. The snore detector according to claim 17, wherein means for processing the pressure signal to provide an approximation of average peak values for the pressure signal:
  (i) calculates, during a current processing cycle n, a current approximation of average peak value C[n] as:

$$C[n]=C[n-1]+W(Y[n]-C[n-1]),$$

responsive to an approximation of the average peak value in a previous processing cycle C[n−1] being greater than the pressure signal during a current processing cycle Y[n], and
  (ii) calculates, during the current processing cycle, the current approximation of average peak value C[n] as:

$$C[n] = C[n-1] - C[n-1]\frac{W}{K_3},$$

responsive to the approximation of the average peak value in a previous processing cycle C[n−1] not being greater than the pressure signal during a current processing cycle Y[n], wherein W is charge constant for an RC circuit, and wherein $K_3$ is a ratio of a charge to discharge rate for the RC circuit.

19. The snore detector according to claim 18, wherein the means for adding the offset to the approximation of average peak values to produce the threshold value T[n] during a current processing cycle add the offset by processing the current approximation of average peak value C[n] as follows:

$$T[n]=K_1 C[n]+K_y,$$

where $K_1$ and $K_y$ are constants.

20. The snore detector according to claim 19, wherein a value of $K_y$ is selected based on the pressure signal.

21. The snore detector according to claim 13, further comprising means for adjusting the pressure provided by the pressure support system based on whether a snore is declared.

22. A threshold setting system that determines a threshold value for a snore detector, the threshold setting system comprising:
  (a) a pressure sensor adapted to generate a pressure signal indicative of a pressure at an airway of a patient that includes frequencies in a qualifying range;

(b) means for processing the pressure signal to provide an approximation of average peak values for the pressure signal, wherein the means for processing the pressure signal to provide the approximation of average peak values for the pressure signal also:

(1) calculates, during a current processing cycle n, a current approximation of average peak value C[n] as:

$$C[n]=C[n-1]+W(Y[n]-C[n-1]),$$

responsive to an approximation of the average peak value in a previous processing cycle C[n−1] being greater than the pressure signal during a current processing cycle Y[n], and (2) calculates, during the current processing cycle, the current approximation of average peak value C[n] as:

$$C[n] = C[n-1] - C[n-1]\frac{W}{K_3},$$

responsive to the approximation of the average peak value in a previous processing cycle C[n−1] not being greater than the pressure signal during a current processing cycle Y[n], wherein W is charge constant for an RC circuit, and wherein $K_3$ is a ratio of a charge to discharge rate for the RC circuit; and (c) means for adding an offset to the approximation of average peak values to produce the threshold value.

23. The system according to claim 22, wherein the means for adding the offset to the approximation of average peak values to produce the threshold value T[n] during a current processing cycle adds the offset by processing the current approximation of average peak value C[n] as follows:

$$T[n]=K_1C[n]+K_y,$$

where $K_1$ and $K_y$ are constants.

24. The system according to claim 23, wherein a value of $K_y$ is selected based on the pressure signal.

* * * * *

UNITED STATES PATENT AND TRADEMARK OFFICE
CERTIFICATE OF CORRECTION

PATENT NO. : 7,246,619 B2
APPLICATION NO. : 10/265845
DATED : July 24, 2007
INVENTOR(S) : Truschel et al.

It is certified that error appears in the above-identified patent and that said Letters Patent is hereby corrected as shown below:

Column 14; line 53 should read: $C[n] = C[n-1] + W(Y[n] - C[n-1]$

Signed and Sealed this

Twenty-seventh Day of November, 2007

JON W. DUDAS
*Director of the United States Patent and Trademark Office*